(12) United States Patent
Allred et al.

(10) Patent No.: US 6,997,708 B2
(45) Date of Patent: *Feb. 14, 2006

(54) TREATMENT COMPOSITIONS AND STRIPS HAVING A SOLID ADHESIVE LAYER AND TREATMENT GEL ADJACENT THERETO

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/728,525

(22) Filed: Dec. 5, 2003

(65) Prior Publication Data

US 2005/0089820 A1 Apr. 28, 2005

Related U.S. Application Data

(63) Continuation-in-part of application No. 10/692,117, filed on Oct. 22, 2003.

(51) Int. Cl.
*A61C 17/00* (2006.01)
*A61C 5/00* (2006.01)

(52) U.S. Cl. ........................................ 433/80; 433/215
(58) Field of Classification Search ................ 433/80, 433/215, 216; 424/53; 206/63.5, 369
See application file for complete search history.

(56) References Cited

U.S. PATENT DOCUMENTS

| | | | |
|---|---|---|---|
| 165,584 A | 7/1875 | Hopfen | |
| 1,637,153 A | 7/1927 | Lawton | |
| 2,257,709 A | 9/1941 | Anderson | 128/260 |
| 2,835,628 A | 5/1958 | Saffir | 167/84 |
| 3,339,547 A | 9/1967 | Drabkowski | 128/260 |
| 3,527,219 A | 9/1970 | Greenberg | 128/260 |
| 3,577,460 A | 5/1971 | Lee | 32/32 |
| 3,624,909 A | 12/1971 | Greenberg | 32/40 |

(Continued)

FOREIGN PATENT DOCUMENTS

WO   WO 88/06869   9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Cary E. O'Connor
(74) *Attorney, Agent, or Firm*—Workman Nydegger

(57) ABSTRACT

Treatment compositions in the shape of a strip or patch include a substantially solid adhesive layer and a treatment gel. A barrier layer may be included on an outer surface of the adhesive layer to form a treatment strip. The adhesive layer comprises a substantially solid adhesive composition that has increased adhesiveness to oral tissue when moistened with saliva or water. The adhesive layer is formed from an intermediate composition that is heated to drive off the solvent. Using a treatment gel separate from the adhesive layer improves the potency and stability of an active agent that is sensitive to heat, as the treatment gel is typically not heated prior to use like the adhesive layer. The adhesiveness of the treatment composition or strip facilitates placement over a person's teeth. The moistened adhesive composition reliably adheres the treatment composition or strip against a user's teeth during a desired procedure. Because a substantial portion of the adhesive composition remains solid or semi-solid during treatment, the adhesive composition maintains a substantial portion of its adhesive properties and internal cohesive strength compared to, e.g., a treatment gel used by itself.

57 Claims, 4 Drawing Sheets

U.S. PATENT DOCUMENTS

| | | | |
|---|---|---|---|
| 3,688,406 A | 9/1972 | Porter et al. | 32/40 R |
| 3,955,281 A | 5/1976 | Weitzman | 32/14 B |
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettenerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | 424/49 |
| 6,682,721 B1 | 1/2004 | Kim et al. | 424/53 |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

FOREIGN PATENT DOCUMENTS

| | | |
|---|---|---|
| WO | WO 03/000216 | 1/2003 |

TREATMENT COMPOSITIONS AND STRIPS HAVING A SOLID ADHESIVE LAYER AND TREATMENT GEL ADJACENT THERETO

CROSS-REFERENCE TO RELATED APPLICATION

This application is a continuation-in-part of U.S. application Ser. No. 10/692,117, filed Oct. 22, 2003. The foregoing application is incorporated herein in its entirety.

BACKGROUND OF THE INVENTION

1. The Field of the Invention

This invention is in the field of treatment strips used to apply an active agent to a person's teeth and/or gums. More particularly, the invention relates to treatment compositions in the form of a strip or patch that include a substantially solid adhesive layer that becomes adhesive to teeth when moistened (e.g., by moisture or saliva on a user's teeth) and a treatment gel adjacent to the adhesive layer. The treatment strips may optionally include a moisture-resistant barrier layer adjacent to the adhesive layer.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with making customized trays, less time consuming and costly alternatives have been developed. Contrary to marketing campaigns, however, many alternatives have substantial disadvantages, primarily in terms of their effectiveness (or lack thereof) in actually bleaching teeth. They also have their own unique issues relating to difficulty of use, low comfort, and poor taste (bleaching and other oral treatment compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental trays that can be self-customized (e.g., so-called "boil-and-bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel of moderate viscosity and relatively low stickiness on the side of the strip facing the user's teeth. To install the bleaching strip, a portion of the bleaching strip is first placed over the front surfaces of the user's teeth, followed by folding the remainder of the strip around the occlusal edges of the teeth and back against a portion, of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk and maintain the bleaching strips properly oriented over the teeth to be bleached.

Even if a user successfully maintains a conventional bleaching strip in its proper position during the recommended bleaching period, the bleaching often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In practical terms, the use of conventional bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are the least prone to move is at night while the person is sleeping. Unfortunately, it is recommended that conventional bleaching strips not be used while sleeping, presumably to prevent accidental choking on an inadvertently dislodged bleaching strip. This only confirms the tendency of conventional bleaching strips to easily dislodge from a user's teeth.

Ultimately, the main impediment to successful bleaching is the failure of users to a complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes a user to become discouraged before desired results are attained.

In view of the foregoing, there is an ongoing need for improved bleaching apparatus and methods that are simple and easy to use, that reliably remain in position over the user's teeth so as to reduce diffusion of bleaching composition into a user's oral cavity. Such improvements would be expected to improve or encourage compliance by the user.

BRIEF SUMMARY OF THE PREFERRED EMBODIMENTS

The present invention generally relates to improved treatment compositions in the form of a strip or patch used to treat a person's teeth and/or gums. Treatment strips according to the invention include an adhesive layer comprising a substantially solid adhesive composition that becomes more adhesive to teeth when moistened (e.g., by saliva or water), and a treatment gel adjacent to the adhesive layer. The treatment gel includes an active agent for treating teeth and/or gums and may comprise a bead, a continuous layer, or a plurality of discontinuous regions or islands.

In one embodiment, treatment strips according to the invention include a moisture-resistant barrier layer, such as a thin, flexible membrane having no predefined shape. To the extent that a barrier layer is subsequently applied or attached to an existing treatment composition comprising an adhesive layer and treatment gel, the treatment composition may be considered as an intermediate to a finished treatment strip comprising the treatment composition and barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester, polyurethane, or similar moisture-resistant material. The barrier layer may be as simple as a layer of a moisture resistant barrier-forming material that is sprayed or painted on, applied by dipping, or otherwise applied to an existing adhesive layer comprising a substantially solid adhesive composition (e.g., one that is in the form of a strip or patch).

The substantially solid adhesive composition forming the adhesive layer comprises at least one tooth adhesion agent that contributes or provides increased adhesiveness to teeth when moistened by saliva or water, and optionally at least one active agent. When placed over a person's teeth and/or gums, the adhesive composition reliably adheres to the teeth and/or gums, thereby maintaining reliable contact between the treatment gel and a person's teeth and/or gums to be treated. A barrier layer is advantageously provided to protect the adhesive layer and treatment gel from diffusing away from the person's teeth into the oral cavity as a result of ambient saliva or moisture found within the person's mouth.

The adhesive layer comprises a substantially solid, coherent adhesive composition, as opposed to a liquid, gel, or dry particulate or powdery composition. As such, the adhesive layer advantageously comprises one or more coherent regions or masses of a substantially solid adhesive composition that do not readily run or flow. A substantially solid and coherent adhesive layer in combination with a treatment gel better adheres to a person's teeth and does not readily diffuse into the surrounding oral cavity on its own, absent becoming diluted by saliva or moisture in a person's mouth, compared to a treatment gel used by itself. This helps maintain the adhesive composition and treatment gel between the optional barrier layer and a person's teeth being bleached and helps prevent diffusion of the active agent into the surrounding oral cavity. This, in turn, promotes better tooth and/or gum treatment, patient compliance, and reduces the tendency of the user to taste the treatment composition when in use.

The tooth adhesion agent within the adhesive layer contributes or provides increased adhesiveness to teeth when moistened with saliva or water. In one embodiment, the tooth off adhesion agent advantageously remains substantially non-adhesive when the adhesive composition is in a dry or substantially solid condition, but becomes adhesive to teeth when moistened with, e.g., water or saliva. A non-limiting example of a suitable tooth adhesion agent is polyvinyl pyrrolidone (PVP), although it is within the scope of the invention to use other tooth adhesion agents known in the art.

The adhesive composition, as well as intermediate compositions used to make the substantially solid adhesive composition, may include other components as desired to yield a final composition having desired properties. These include both inert components and active agents. Examples of inert components include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), flavorants, sweeteners, and the like.

Examples of active agents include bleaching agents (e.g., hydrogen peroxide or solid complexes or analogues of hydrogen peroxide, such as carbamide peroxide or sodium perborate), bleaching agent activators (e.g., metals, metal salts, and bases), desensitizing agents (e.g., potassium nitrate), remineralizing agents (e.g., sodium fluoride or other fluoride salts), antimicrobial agents (e.g., chlorhexidine, troclosan, and tetracycline), antiplaque agents, anti-tartar agents, or other medicaments.

In one embodiment, the dental treatment gel comprises an active agent and a tackifying agent, typically dispersed within a liquid carrier or vehicle. Examples of active agents include bleaching agents, desensitizing agents, remineralizing agents, antimicrobial agents, antiplaque agents, and anti-tartar agents. Exemplary dental bleaching agents include aqueous hydrogen peroxide, carbamide peroxide, sodium perborate, sodium percarbonate, and the like. It is, of course, within the scope of the invention to use any dental bleaching agent known in the art.

Exemplary tackifying agents include PVP, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like. It is, of course, within the scope of the invention to use any tackifying agent known in the art.

Exemplary liquid carriers or vehicles include water, alcohols, polyols (e.g., glycerin, sorbitol, polyethylene glycol, propylene glycol, and polypropylene glycol), and the like.

According to one embodiment, the substantially solid adhesive composition is made by first forming a flowable liquid or gel adhesive composition intermediate that is subsequently dried to form a substantially solid adhesive layer. This may be performed by heating or otherwise causing one or more volatile solvents to be driven off by evaporation, thus leaving behind a substantially solid adhesive composition or layer. The drying process may be performed before or after the adhesive composition intermediate is placed into contact with a barrier layer. In one embodiment, the adhesive intermediate composition is cast onto a forming surface, dried and removed to yield a substantially solid sheet that is stamped or otherwise formed into a desired shape. Thereafter, a treatment gel is attached or applied to an inner surface of the adhesive layer and a barrier layer is optionally applied or attached to an outer surface of the adhesive layer. The treatment gel can be applied to the adhesive layer before or after the barrier layer, or in the absence of a barrier layer. The adhesive layer can be formed and dried on an existing polymer sheet and then used as is to form treatment strips or separated from the sheet to form a treatment composition.

An advantage of providing a treatment gel that is separate from the adhesive layer, rather than an active agent that is contained within the adhesive layer, is that it provides a treatment composition or strip that is more stable or consistent relative to the amount of active agent, particularly where the active agent is sensitive to heat. Heating the adhesive composition intermediate to drive off the water so as to yield a substantially solid adhesive composition can destabilize a bleaching agent or other heat-sensitive active agent contained therein and cause it to become less potent. Because the treatment gel is generally not heated during manufacture of treatment composition and strips according to the invention, greater stability and potency of a heat-sensitive active agent can be achieved.

In yet another embodiment, a barrier layer can be coated with a flowable adhesive composition intermediate, such as by painting or spreading, which is then heated or allowed to dry at room temperature to form the substantially solid adhesive layer. The treatment gel may then be applied to the exposed surface of the adhesive layer.

The size and shape of treatment compositions and strips according to the invention can be tailored to more readily fit a person's upper or lower dental arch. They may also be tailored to fit persons having differently-sized or shaped dental arches. The treatment compositions and strips are advantageously designed so as to substantially cover the front and lingual surfaces of the teeth and/or gums to be treated. Treating both the front and lingual surfaces helps in treating the interproximal spaces between adjacent teeth. The treatment compositions and strips are advantageously flexible and adhesive so as to readily conform to a wide variety of differently-sized teeth and dental arches.

The treatment compositions and strips according to the invention can be designed to be worn for any desired time period. Increasing the concentration of active agent within the treatment gel generally reduces the required treatment time. Nevertheless, due to the extremely comfortable fit and reliable adhesion between the inventive treatment compositions and strips and the person's teeth, it is possible to wear such compositions and strips for extended periods of time in order to ensure even and thorough treatment. Treatment compositions and strips according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive treatment devices such as large, bulky dental appliances.

The treatment compositions and strips can be designed to be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional treatment or overnight treatment while a person is sleeping, may last from about 2 hours to about 12 hours. Treatment sessions may be repeated as many times as are needed to obtain a desired degree of treatment. In the case of tooth bleaching, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple treatment compositions or strips may be packaged together and sold as a kit. In one embodiment, the number of treatment compositions or strips provided with each kit can equal the number of sessions that represent a prescribed treatment regimen. Because the treatment compositions and strips are generally flat or low profile, multiple treatment compositions or strips can be stacked or laid together within a package. The treatment compositions or strips can be sealed collectively or individually as desired. They may contain a removable protective layer on their interior surfaces to protect the adhesive layer and the treatment gel from contamination or moisture, both of which can possibly cause premature decomposition or degradation of the active agent.

It is within the scope of the invention to provide barrier layers, adhesive layers, and a treatment gel that are initially separate and that are brought together by the end user. The adhesive composition of the adhesive layer may be a dry or substantially solid strip or patch, or it may be a liquid or gel that is applied to a barrier layer and allowed to dry or harden prior to placement of the treatment gel adjacent to the adhesive layer and placement of the finished treatment strip over the person's teeth and/or gums.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
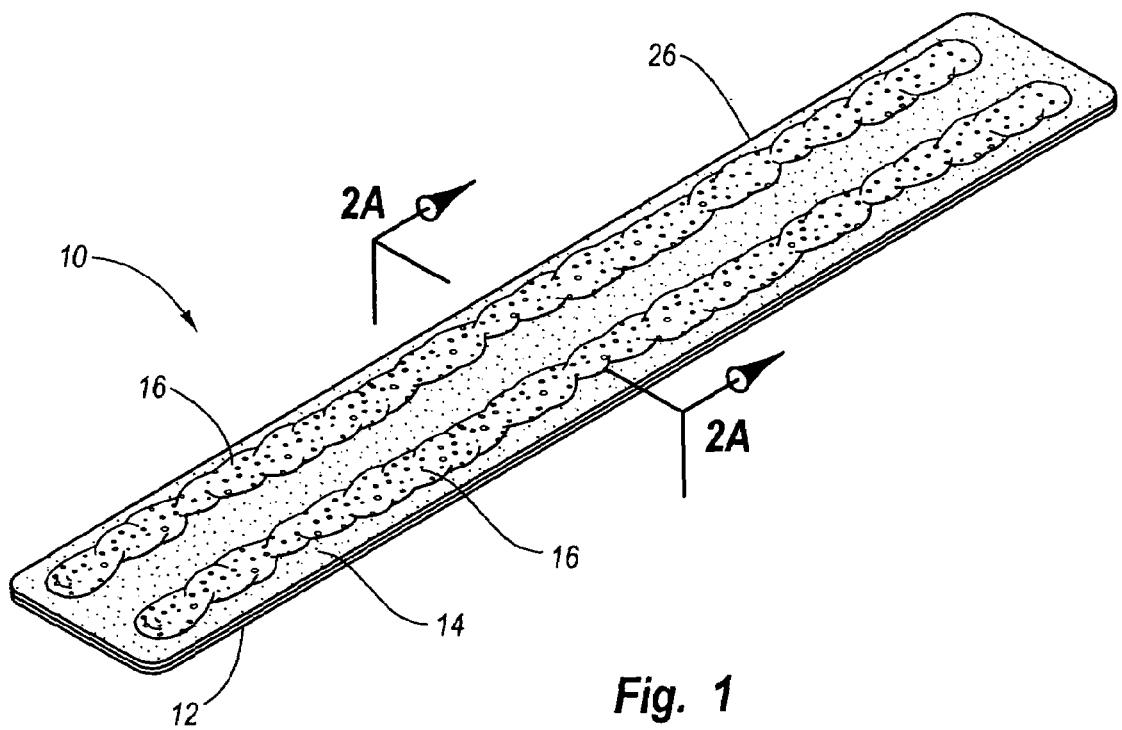
FIG. 1 is a perspective view of an exemplary treatment strip according to the invention that comprises a barrier layer, an adhesive layer, and a treatment gel.

The present invention generally relates to improved treatment compositions and strips used to treat a person's teeth and/or gums. The inventive treatment compositions include an adhesive layer that becomes more adhesive to teeth when moistened with water or saliva and a treatment gel adjacent to the adhesive layer. In one embodiment, treatment strips according to the invention include a moisture-resistant barrier layer, an adhesive layer that becomes more adhesive to teeth when moistened with water or saliva, and a treatment gel adjacent to the adhesive layer. When the treatment composition or strip is placed over a person's teeth, the adhesive layer reliably adheres to the teeth, allowing the treatment gel to remain in contact with the teeth and/or gums to be treated. The optional barrier layer protects the adhesive layer and treatment gel from diffusing away from the person's teeth as a result of ambient saliva or moisture found within the person's mouth.

The inventive treatment compositions and strips are more adhesive to teeth than conventional dental bleaching strips. Such compositions and strips are also less intrusive than bulky, over-the-counter, non-custom or boil-and-bite dental trays. In some ways they are as reliable, or even more reliable, than custom-fitted dental trays in maintaining a treatment gel against a person's teeth. In some cases, they are also as comfortable, or even more comfortable, than custom-fitted trays.

The term "barrier layer", as used herein, refers to one or more layers of a moisture-resistant material that protects the adhesive layer and treatment gel from ambient moisture and saliva found within a person's mouth when the treatment strip is placed over the person's teeth. The barrier layer may also serve to protect the adhesive layer and treatment gel from moisture or other contaminants during storage and prior to use. The barrier layer may be in any desired form including, but not limited to, a sheet laminated to a surface of the adhesive layer or a coating applied to a pre-formed adhesive layer or treatment composition.

The term "adhesive layer", as used herein, refers to one or more regions of an adhesive composition that has been formulated or processed so as to be substantially solid, coherent, and non-flowable. The adhesive layer may comprise a single continuous region or layer adjacent to the treatment gel and, optionally, a barrier layer, or it may comprise a plurality of discontinuous regions or layers adjacent to a barrier layer and spaced-apart by random or predetermined intervals.

The term "substantially solid", as used herein, refers to an adhesive composition or layer that is in a solid or semi-solid condition. In one aspect, a "substantially solid" adhesive composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of an adhesive composition or layer, also excludes dry particulate adhesive compositions or powders because dry particulates and powders readily flow when subjected to gravity and/or are readily separated (i.e., the particles as a whole have little or no internal cohesion). Moreover, powders or particulates, when viewed as a whole, are not coherent or solid.

One characteristic of the "substantially solid" adhesive compositions or layers is that they become more adhesive when an exposed surface thereof is moistened with, e.g., saliva or water. When moistened, the surface of the adhesive composition or layer turns into a sticky material that is able to more strongly adhere to teeth compared to a substantially solid adhesive composition or layer that has not been moistened. The adhesive composition at the surface may become a viscous liquid, paste or gel, at least temporarily, depending on the amount of moisture that is applied to the surface of the "substantially solid" adhesive composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" adhesive composition or layer over time (e.g., during a procedure in which the adhesive layer is protected from saliva and ambient moisture in a person's mouth by a moisture-resistant barrier layer).

The term "treatment gel", as used herein, refers to a treatment composition that has been formulated or processed so as to be flowable (e.g., it can be expressed out of a syringe orifice or other dispensing means known in the art). The treatment gels according to the invention are, however, preferably sufficiently thick or viscous that they will not run off an adhesive layer onto which the treatment gel is placed. In one embodiment, the treatment gel is rubbery or highly viscous. When a treatment gel is placed next to a dry adhesive layer, the two dissimilar compositions may tend to reach an equilibrium wherein some of the moisture or other liquid carrier of the treatment gel diffuses into the adhesive layer, thus further increasing the viscosity and stiffness of the treatment gel. The treatment gel may comprise a single continuous bead or layer adjacent to the adhesive layer, or it may comprise a plurality of discontinuous regions or layers spaced-apart by random or predetermined intervals.

The terms "strip" or "patch" are used interchangeably and shall refer to any treatment composition or device that is substantially flat, or that has a curvature or bend but that does not constitute a "dental tray", as that term is understood in the art. A "strip" or "patch", with or without a barrier layer, includes an inner surface or region configured to engage the front and/or rear surfaces of a person's teeth and/or gums when in use and an outer surface that is generally oriented away from the person's teeth and/or gums. A "strip" or "patch" may be configured so that a portion of the inner surface engages the incisal or occlusal edges of the person's teeth when in use. The strip or patch may be curved or straight in one or both of the lengthwise and widthwise directions in order to fit over a user's teeth and/or gums in a desired manner.

The term "molecular weight", as used herein, shall refer to number average molecular weight expressed in Dalton, unless otherwise specified.

II. Treatment Compositions and Strips

The treatment compositions according to the invention can exist alone or in combination with a barrier layer as part of a treatment strip. Treatment compositions according to the invention include an adhesive layer that becomes more adhesive to teeth when moistened by, e.g., saliva or water, and a treatment gel adjacent to an inner surface of the adhesive layer. A moisture-resistant barrier layer adjacent to an outer surface of the adhesive layer protects the adhesive layer and treatment gel from ambient moisture within a person's mouth during use. Following are preferred examples of barrier layers, adhesive layers, and treatment gels according to the invention, as well as characteristics of treatment compositions or strips made therefrom.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, polyesteramides, or blends thereof. Such materials may be provided in the form of flat, flexible sheets to which an adhesive composition or layer is applied. Alternatively, such sheets may be applied or attached to an existing adhesive composition or a treatment composition comprising a substantially solid adhesive layer and a treatment gel.

Notwithstanding the foregoing, it is within the scope of the invention to provide barrier layers having any desired material, thickness or rigidity so long as the barrier layer provides at least some moisture protection relative to the adhesive composition or layer and treatment gel. The barrier layer may be as simple as a layer of a moisture resistant material that is sprayed or painted on, applied by dipping, or otherwise applied to an existing adhesive or treatment composition (e.g., one that is in the form of a strip or patch).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. Plasticizers, flow additives, and fillers known in the art can be used as desired to modify the properties of any of the foregoing polymers used to form the barrier layer.

As will be discussed below, some solid adhesive compositions are more adhesive to polymer materials comprising the barrier layer than others, often depending on the tooth adhesion agent that is used. It has been found that, as between polyethylene, paraffin and polyethylene terephthalate, substantially solid adhesive compositions tend to adhere more strongly to polyethylene terephthalate, particularly MYLAR.

It is also within the scope of the invention to utilize barrier layers that are formed onto a surface of a previously formed adhesive layer or treatment composition, such as by adhering a moisture resistant sheet to the adhesive layer, either alone or that forms part of a treatment composition. Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Adhesive Layers

Prior to being moistened in preparation for or during use, adhesive layers within treatment compositions and strips according to the invention preferably comprise a substantially solid and coherent adhesive composition, as opposed to a liquid, a flowable gel, or a dry powder or particulate. The adhesive layer may comprise a single coherent mass or region, or it may comprise a plurality of coherent masses or regions of a substantially solid adhesive composition. Providing a substantially solid and coherent adhesive layer better maintains the treatment gel against the teeth and/or gums being treated instead of diffusing into the surrounding oral cavity, as compared to treatment gels that are loaded without an adhesive layer into customized or non-customized dental trays or that are applied using a flexible strip of plastic without an adhesive layer. This, in turn, promotes better treatment of the teeth and/or gums and patient compliance by, e.g., reducing irritation to surrounding oral tissues and/or at least some of the bad taste normally associated with treatment compositions.

Substantially solid adhesive compositions that comprise the adhesive layer include at least one tooth adhesion agent and, optionally, one or more inert component or active agents. In the case where an active agent is included, it may be advantageously dispersed within a substantially solid matrix comprising the tooth adhesion agent. Alternatively, an active agent in the form of a liquid or solution can be spread, sprayed or otherwise applied to the inner surface of the adhesive composition prior to or after applying the treatment gel thereto. Following are preferred tooth adhesion agents, as well as exemplary inert components and active agents that may optionally be included within the adhesive composition.

1. Tooth Adhesion Agents

The tooth adhesion agent may comprise any known tackifying agent that is substantially non-adhesive, or less adhesive, when the adhesive composition or layer is substantially solid, but which becomes more adhesive to teeth when the adhesive composition or layer is moistened with, e.g., water or saliva. A presently preferred tooth adhesion agent is polyvinyl pyrrolidone (PVP). PVP polymers have been found to provide excellent adhesion to polymer barrier layers made from PE, PET, polyurethane, and paraffin, to be substantially non-adhesive when the adhesive composition is dry to the touch, and to have superior adhesion to teeth when a surface of a substantially solid adhesive composition is moistened with saliva or water.

Non-limiting examples of polyvinyl pyrrolidone polymers that have been used in formulating adhesive compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid adhesive compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid adhesive composition (exclusive of any bound water or other solvent), more preferably in a range of about 20% to about 80% by weight of the substantially solid adhesive composition, and most preferably in a range of about 40% to about 75% by weight of the substantially solid adhesive composition.

2. Inert Components

The adhesive compositions and layers may include inert components in addition to the tooth adhesion agent, as desired, to yield a final composition or layer having desired properties. Examples of "inert" components include, but are not limited to, plasticizers and humectants (e.g., glycerin, sorbitol, polyethylene glycol, propylene glycol, and polypropylene glycol), volatile solvents (e.g., water and alcohols, such as ethanol), neutralizing agents (e.g., sodium hydroxide), thickening agents (e.g., fumed silica), flavorants, sweeteners, and the like.

When water is used as a solvent when manufacturing adhesive compositions or layers according to the invention and then driven off by evaporation to yield a substantially solid dental bleaching or desensitizing composition, it is postulated that a significant amount of water remains bound or associated with the hydrophilic components within the adhesive composition, including the tooth adhesion agent, any inert components (e.g., polyols added as humectants, stabilizing agents, neutralizing agents, and/or thickening agents), and any hydrophilic active agents (e.g., bleaching and/or desensitizing agents). Although the amount of residual water has not yet been determined, it is believed that approximately 10% of the water added initially remains after the initially flowable adhesive composition intermediate has been dried sufficiently to yield the substantially solid adhesive composition or layer.

3. Active Agents

A wide variety of active agents known in the dental and oral arts can be included within the adhesive composition or layer. Examples of include bleaching agents (e.g., hydrogen peroxide or solid complexes or analogues of hydrogen peroxide, such as carbamide peroxide or sodium perborate), desensitizing agents (e.g., potassium nitrate), remineralizing agents (e.g., sodium fluoride or other fluoride salts), antimicrobial agents (e.g., chlorhexidine, troclosan, and tetracycline), antiplaque agents, anti-tartar agents, other medicaments, bleaching agent stabilizers (e.g., EDTA, sodium lauryl sulfate, sodium stannate, alkali metal pyrophosphates, tartrates, phenylphosphonic acid, and citric acid), and bleaching agent activators (e.g., metals, metal salts, and bases).

Examples of substantially solid adhesive compositions and layers that include one or more active agents are disclosed in U.S. application Ser. No. 10/446,235, filed May 27, 2003; U.S. application Ser. No. 10/446,471, filed May 27, 2003; U.S. application Ser. No. 10/637,237, filed Aug. 8, 2003; U.S. application Ser. No. 10/646,484, filed Aug. 22, 2003; and U.S. application Ser. No. 10/646,443, filed Aug. 22, 2003. For purposes of disclosing solid adhesive compositions and layers that include one or more active agents, the foregoing applications are incorporated herein by reference.

When one or more bleaching agents are included within the substantially solid adhesive composition, they are preferably included in an amount in a range of about 5% to about 80% by weight of the substantially solid adhesive composition, more preferably in a range of about 10% to about 60% by weight of the substantially solid adhesive composition, and most preferably in a range of about 20% to about 50% by weight of the substantially solid adhesive composition.

When potassium nitrate is included within the substantially solid adhesive composition as a desensitizing agent, it is preferably included in an amount in a range of about 0.01% to about 50% by weight of the substantially solid adhesive composition, more preferably in a range of about 0.1% to about 25% by weight of the substantially solid adhesive composition, and most preferably in a range of about 0.5% to about 10% by weight of the substantially solid adhesive composition.

When included in combination with a dental bleaching agent, potassium nitrate is preferably included in an amount in a range of about 0.01% to about 2% by weight of the substantially solid adhesive composition, more preferably in a range of about 0.05% to about 1% by weight of the substantially solid adhesive composition, and most preferably in an amount of about 0.5% by weight of the substantially solid adhesive composition. It has been found that including potassium nitrate in these amounts creates a synergistic effect with the dental bleaching agent that appears to enhance tooth whitening. It also provides the highest level of tooth desensitization when used with a bleaching agent.

For treating periodontal disease, chlorhexidine gluconate is a preferred medicament and is preferably included in an amount in a range of about 0.01 to about 50% by weight of the substantially solid adhesive composition, more preferably in a range of about 0.05% to about 25% by weight of the substantially solid adhesive composition, and most preferably in a range of about 0.1% to about 10% by weight of the substantially solid adhesive composition. Other antibacterial agents or medicaments may be included in the same concentration ranges.

C. Treatment Gels

The treatment compositions and strips according to the invention may include any treatment gel known in the art. The treatment gel may comprise a continuous layer positioned so as to cover a person's front tooth and/or gum surfaces, rear tooth and/or gum surfaces, or combinations thereof, or it may comprise separate beads, layers or islands of gel separated by a space. Preferred treatment gels are those that are substantially viscous and tacky in order to assist the adhesive layer in retaining the treatment composition or strip against a person's teeth and/or gums during use. In one aspect of the invention, the treatment gels according to the invention may comprise at least one active agent and any of the adhesive composition intermediates used to manufacture the substantially solid adhesive compositions or layers described herein.

Exemplary dental treatment gels, and methods for making such gels, which may be used to manufacture the treatment compositions and strips according to the invention are disclosed in U.S. Pat. No. 5,376,006; U.S. Pat. No. 5,770,182; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; and U.S. Pat. No. 6,503,485. For purposes of disclosing dental treatment gels, and methods of making such gels, the foregoing patents are incorporated herein by reference.

In general, the treatment gels will include at least one active agent, at least one tackifying agent, and a liquid or gel carrier or vehicle into which the active agent and tackifying agent are dispersed. An advantage of providing a treatment gel separate from the adhesive layer is that it provides a treatment composition or strip that is more stable or consistent relative to the amount of active agent, at least in the case where the active agent is sensitive to heat. Heating an adhesive composition intermediate to drive off the water so as to yield a substantially solid adhesive composition can destabilize or decompose an active agent that is sensitive to heat and render it less potent. Because the treatment gel is generally not heated during manufacture of treatment composition and strips according to the invention, greater stability and potency of the active agent may be achieved. Following are preferred active agents, tackifying agents, and carriers or vehicles.

1. Active Agents

In one embodiment, the active agent comprises at least one dental bleaching agent. A common dental bleaching agent that is known to bleach teeth and that has been found to be safe for oral use is hydrogen peroxide. However, hydrogen peroxide does not itself exist free in nature, but only as an aqueous solution or as a complex. Aqueous hydrogen peroxide is an acceptable dental bleaching agent to the extent that an anhydrous bleaching gel is not desired. Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the treatment gels according to the invention can have any desired concentration, e.g., between 1–90% by weight of the treatment gel. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

In the case of a treatment gel used to bleach teeth, the one or more bleaching agents are preferably included in an amount in a range of about 1% to about 60% by weight of the treatment gel, more preferably in a range of about 3% to about 40% by weight of the treatment gel, and most preferably in a range of about 5% to about 30% by weight of the treatment gel.

Instead of, or an addition to a dental bleaching agent, the treatment gels according to the invention may include one or more other active agent as desired to yield a treatment gel having desired properties. Examples of other active agents include desensitizing agents (e.g., potassium nitrate, other potassium salts, citric acid, citrates, and sodium fluoride), antimicrobial agents, remineralizing agents, antiplaque agents, anti-tartar agents, and other medicaments known in the art.

Exemplary antimicrobial agents that can be used to treat gingivitis, periodontal disease, plaque or other oral bacterial infections or maladies include, but are not limited to, chlorhexidine gluconate, cetylpyridinium chloride, phenol, minocycline, tetracycline, doxycycline, penicillin, clindamycin, ciprofloxacin, metronidazole, and tricolsan. Exemplary remineralizing agents capable of preventing caries include, but are not limited to, sodium fluoride, sodium monofluorophosphate, stannous fluoride, other fluoride salts, and calcium phosphate. Exemplary anti-tartar agents include, but are not limited to, pyrophosphates, polypyrophosphates, polyvinyl methyl ether malic acid, sodium hexametal phosphate, alkali metal phosphates, calcium lactate, and triclosan. Exemplary anticalculus or antiplaque agents include, but are not limited to, 8-hydroxyquinoline sulfate, dicitrate cyclic ester, and zinc citrate.

When potassium nitrate is included within the treatment gel as a desensitizing agent, it is preferably included in an amount in a range of about 0.01% to about 50% by weight of the treatment gel, more preferably in a range of about 0.1% to about 25% by weight of the treatment gel, and most preferably in a range of about 0.5% to about 10% by weight of the treatment gel.

When potassium nitrate is included in combination with a dental bleaching agent, the potassium nitrate is preferably included in an amount in a range of about 0.01% to about 2% by weight of the treatment gel, more preferably in a range of about 0.05% to about 1% by weight of the treatment gel, and most preferably in an amount of about 0.5% by weight of the treatment gel. It has been found that including potassium nitrate in these amounts creates a synergistic effect with the dental bleaching agent that appears to enhance tooth whitening. It also provides the highest level of tooth desensitization when used with a bleaching agent.

When treating periodontal disease, chlorhexidine gluconate is a preferred medicament and is preferably included in an amount in a range of about 0.01 to about 50% by weight of the treatment gel, more preferably in a range of about 0.05% to about 25% by weight of the treatment gel, and most preferably in a range of about 0.1% to about 10% by weight of the treatment gel. Other anti-bacterial agents or medicaments may be included in the same concentration ranges.

2. Tackifying Agents

Useful tackifying agents that may be used in the treatment gel include any of the tooth adhesion agents disclosed herein for use in manufacturing the substantially adhesive compositions or layers according to the invention. The main difference between a "tackifying agent" within a "treatment gel", and a "tooth adhesion agent" within an "adhesive composition" or "adhesive layer" is the physical state. On the one hand, a tackifying agent within a treatment gel is already mixed with a liquid or gel carrier or vehicle such that the resulting dental treatment gel is immediately sticky and tacky to the touch as a result of the tackifying agent. On the other hand, an adhesive composition or layer typically becomes much more adhesive to teeth when the adhesive composition or layer is moistened by saliva or water as a result of the tooth adhesion agent. The adhesive composition or layer may initially be non-adhesive and dry to the touch prior to moistening with saliva or water.

One useful tackifying agent is polyvinyl pyrrolidone (PVP). Non-limiting examples of polyvinyl pyrrolidone polymers that have been used in formulating treatment gels according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

Other useful tackifying agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

The one or more tackifying agents are preferably included in an amount in a range of about 1% to about 50% by weight of the treatment gel, more preferably in a range of about 3% to about 30% by weight of the treatment gel, and most preferably in a range of about 5% to about 20% by weight of the treatment gel.

3. Carriers and Vehicles

The treatment gel will typically include one or more liquid or gel carriers or vehicles into which the active agent, tackifying agent, and other components are dispersed. Examples of liquid or gel carriers or vehicles include, but are not limited to, water, alcohols (e.g., ethyl alcohol), and polyols (e.g., glycerin, sorbitol, polyethylene glycol, polyethylene oxide, propylene glycol, and polypropylene glycol). The carrier or vehicle will typically comprise the balance of components in the treatment gel in addition to the active agent, tackifying agent, and any other components.

4. Other Components

The treatment gels according to the invention may optionally include other components as desired to yield a treatment gel having desired properties. Examples include bleaching agent stabilizers agents (e.g., EDTA, sodium lauryl sulfate, sodium stannate, alkali metal pyrophosphates, tartrates, phenylphosphonic acid, and citric acid), neutralizing agents (e.g., sodium hydroxide), thickening agents (e.g., fumed silica), flavorants, sweeteners, and the like.

D. Characteristics of Treatment Compositions and Strips

The treatment compositions and strips according to the invention are preferably in the shape of a strip or patch. Treatment compositions and strips that have a substantially solid adhesive layer that becomes more adhesive when moistened with water or saliva are easier to install over a person's teeth and/or gums compared to conventional bleaching strips, which do not reliably adhere to a user's teeth. That is because the inventive treatment compositions and strips are designed to more reliably adhere and remain in place over the person's teeth compared to conventional bleaching strips, which employ a dental bleaching gel immediately adjacent to a plastic sheet. The result is more effective treatment and better patient compliance. In contrast to conventional bleaching strips, which are not recommended for use while a person eats, drinks, smokes or sleeps, treatment compositions and strips according to the invention can be designed so as to be worn while talking, sleeping, eating, drinking, smiling, frowning, grimacing, yawning, coughing, smoking, or making virtually any facial expression or mouth contortion.

Figure 2A:
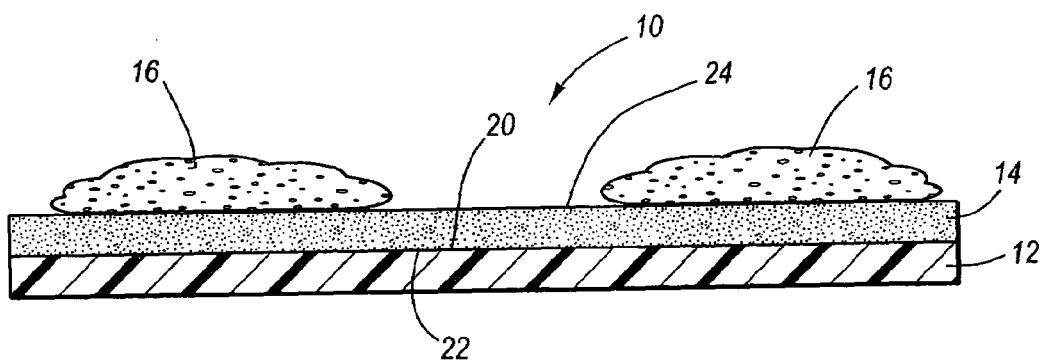
FIG. 2A is a cross-sectional view of the treatment strip depicted in FIG. 1.

An exemplary treatment strip is depicted in FIGS. 1 and 2A. FIG. 1 is a perspective view of a treatment strip 10 comprising a barrier layer 12, which preferably comprises a moisture-resistant material, an adhesive layer 14, which preferably comprises a substantially solid adhesive composition, and a treatment gel 16. As best seen in FIG. 2A, the adhesive layer 14 includes an outer surface 20, which is adjacent to an inner surface 22 of the barrier layer 12, and an inner surface 24, which is adjacent to the treatment gel 16. In one embodiment, both the treatment gel 16 and at least a portion of the inner surface 24 of the adhesive layer 14 are designed to directly contact a person's teeth when the treatment strip 10 is in use. An upper edge 26 of the treatment strip 10 can be designed so as to terminate at or shy of the gingival margin of a person's dental arch when in use.

Figure 2B:
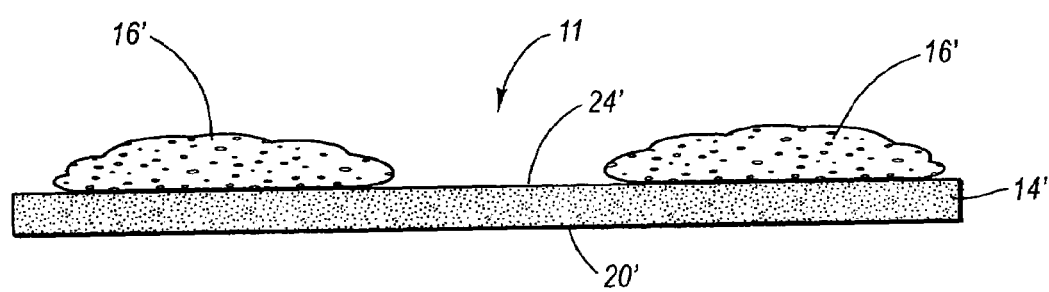
FIG. 2B is a cross-sectional view of en exemplary treatment composition according to the invention in the shape of a strip, but without a barrier layer.

FIG. 2B alternatively depicts a treatment composition 11 comprising an adhesive layer 14' in the shape of a strip or patch, so as to have an outer surface 20' and an inner surface 24', and a treatment gel 16' adjacent to the inner surface 24' of the adhesive layer 14'. The treatment composition 11 differs from the treatment strip 10 of FIGS. 1 and 2A because it includes no barrier layer. Of course, the outer surface 20' of the adhesive layer 14' may optionally be coated with a water-resistant barrier layer or material if desired (see FIG. 2A) to protect the treatment composition 11 (more particularly the adhesive layer 14' and treatment gel 16') from saliva or ambient moisture. The treatment composition 11 may be sold alone or together with a moisture-resistant barrier layer, or a material used to make a barrier layer, that can be placed adjacent to the outer surface 20' of the adhesive layer 14' prior to or during use.

Figure 3:
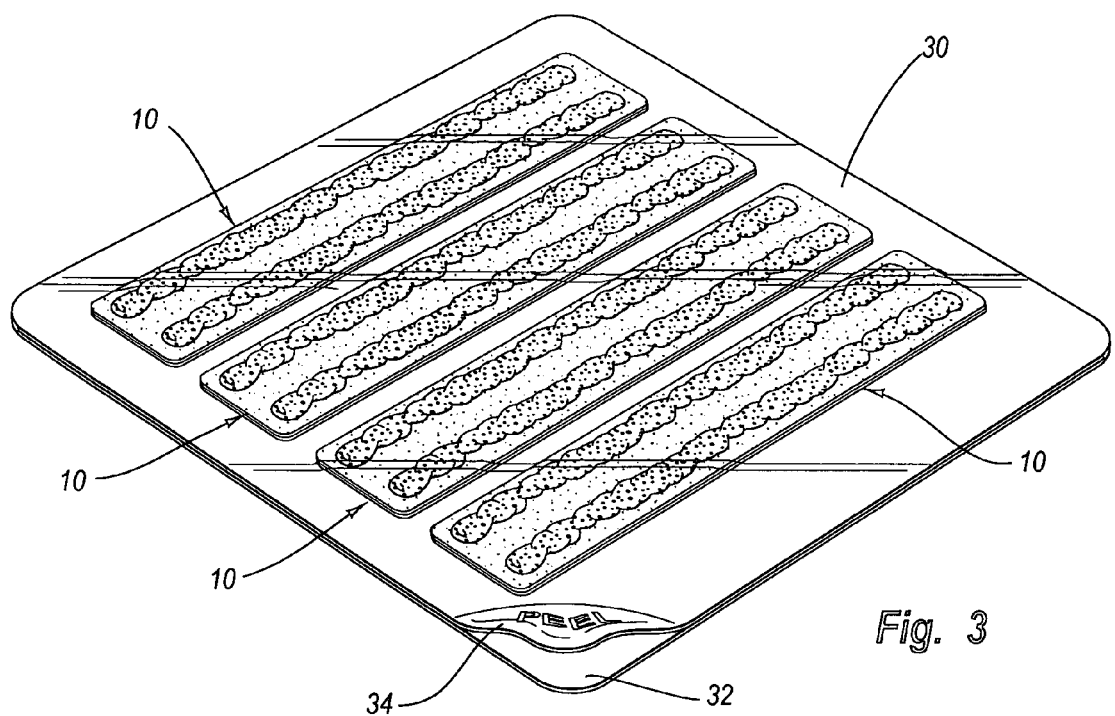
FIG. 3 illustrates a treatment strip (or composition) according to the invention contained within a sealed protective package having a peelable cover.

In order to protect treatment compositions or strips according to the invention from contaminants during storage and prior to use, the treatment compositions or strips can be packaged within a sealed container or package. As illustrated in FIG. 3, one or more treatment strips 10 (or treatment compositions 11) can be sealed within a protective package 30 that includes a rigid support layer 32 and a peelable cover 34. When it is desired to use the treatment strip 10 (or treatment composition 11), the peelable cover 34 is removed and the treatment strip 10 (or treatment composition 11) is removed or separated from the support layer 32. In addition to, or instead of, the protective package 30, the treatment strip 10 (or treatment composition 11) may alternatively include a removable protective layer (not shown) that is temporarily placed adjacent to the treatment gel 16. When it is desired to use the treatment strip 10 (or treatment composition 11), the removable protective layer is removed so as to expose the treatment gel.

Figure 4:
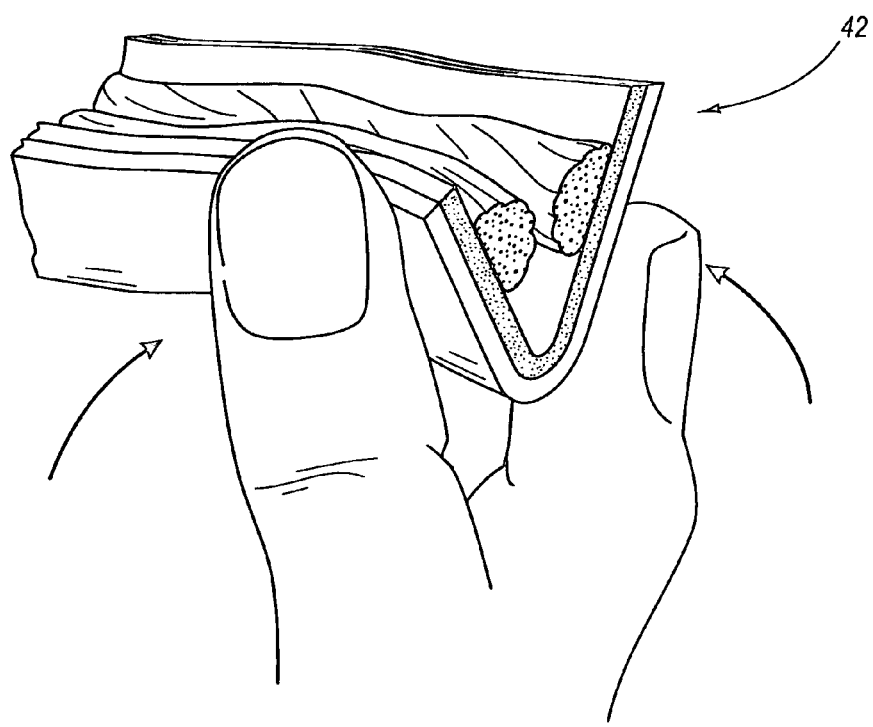
FIG. 4 illustrates a treatment strip according to the invention being manipulated so as to have an approximate V-shaped cross section.

FIG. 4 shows a treatment strip 42 being optionally manipulated (such as by bending, curving or folding) so as to have an approximate V-shaped cross section in order to facilitate placement of the treatment strip 42 over a person's teeth and/or gums.

Notwithstanding the foregoing examples, it will be appreciated that treatment compositions and strips according to the invention can have any shape in the lengthwise and widthwise directions (e.g., they can be straight or curved). In addition, they can be substantially flat, or they may be curved or bent, typically so as to not be what one would consider to be a dental treatment tray.

The size and shape of treatment compositions and strips according to the invention can be tailored to more readily fit either a person's upper dental arch or lower dental arch. They can be sized so as to treat all or merely a subset of a person's teeth. The treatment compositions and strips may be sufficiently adhesive and flexible so as to readily conform to a wide variety of differently-sized teeth and dental arches. The treatment compositions and strips are advantageously designed so as to substantially cover the front and lingual surfaces of the teeth and/or gums to bleached. It is within the scope of the invention to treat more of one surface than another. Treating both the front and lingual surfaces helps to treat the interproximal spaces between a person's teeth.

In general, the thickness of the barrier layer and/or the adhesive layer can be selected to yield a treatment strip having a desired strength and flexibility. In order for the barrier layer to remain flexible so as to conform to a person's teeth, the barrier layer will generally have a thickness ranging from about 0.025 mm to about 1.5 mm, preferably in a range of about 0.05 to about 1 mm. The adhesive layer will generally have a thickness ranging from about 0.1 mm to about 3 mm. The thickness of the adhesive layer can also be selected depending on the intended duration of each treatment session. In general, increasing the thickness of the adhesive layer will provide a longer adhesion of the treatment composition or strip to a person's teeth and/or gums. By way of example, for short wear times, the adhesive layer will preferably have a thickness ranging from about 0.1 mm to about 0.5 mm. For intermediate wear times, the adhesive layer will preferably have a thickness ranging from about 0.5 mm to about 2 mm. For professional use and for overnight treatment, the adhesive layer will preferably have a thickness ranging from about 2 mm to about 3 mm.

The amount of treatment gel within the treatment composition or strip can be selected to yield a treatment composition or strip having a desired tackiness and/or treatment potency. In the case where the adhesive layer includes no active agent, the treatment gel will provide the sum total of the active agent. In such cases, the thickness of the treatment gel may be increased, all things being equal. By contrast, in the case where the adhesive layer also includes an active agent, the treatment gel will not provide all the active agent. In such cases, the thickness of the treatment gel may be decreased, all things being equal.

In addition, the more viscous and tacky the treatment gel, the less deleterious will be the treatment gel on the overall ability of the treatment composition or strip to adhere to a person's teeth. In such cases, the cross-sectional thickness of the treatment gel may be increased, all things being equal. By contrast, the less viscous and tacky the treatment gel, the more deleterious will be the treatment gel on the overall ability of the treatment composition or strip to adhere to a person's teeth. In such cases, the cross-sectional thickness of the treatment gel may be advantageously decreased, all things being equal.

III. Methods of Making Dental Treatment Compositions and Treatment Strips Incorporating such Compositions The various components that make up the inventive treatment compositions and strips according to the invention can be assembled or brought together in any desired order. According to one embodiment, an adhesive composition or layer is first made by forming a flowable adhesive composition intermediate that is then shaped and dried to form a substantially solid adhesive composition or layer in the form of a sheet, strip or patch. This may be performed by heating or otherwise causing one or more volatile solvents to be driven off by evaporation, thus leaving behind the substantially solid adhesive layer. Thereafter, a treatment gel may be placed against an inner surface of the adhesive layer.

An optional barrier layer may also be placed against an outer surface of the adhesive layer in order to protect the adhesive layer and treatment gel from ambient moisture within a person's mouth. The barrier layer may be placed against the adhesive layer either before or after the adhesive composition is dried so as to become substantially solidified. In one embodiment, the barrier layer comprises a thin, flexible sheet. In yet another embodiment, the barrier layer may initially comprise a flowable barrier material or precursor that is later cured or hardened, such as by removing a solvent by evaporation, by chemical or light curing, or by cooling a thermoplastic melt.

In an alternative embodiment, the adhesive intermediate composition can be cast onto a forming surface and dried to form a substantially solid sheet, which is subsequently molded, stamped or otherwise formed into a desired shape. Thereafter, a treatment gel is attached or applied to an inner surface of the adhesive layer, and a barrier layer is optionally applied or attached to an outer surface of the adhesive layer. The treatment gel can be applied to the adhesive layer before or after the barrier layer, or in the absence of a barrier layer.

According to another embodiment, the adhesive layer can be made by spreading a flowable adhesive composition intermediate onto the surface of a large or continuous polymeric sheet (e.g., using a screeding device). The polymeric sheet and adhesive composition intermediate are then placed into a forced air oven or other appropriate desiccation device in order to heat and drive off a substantial portion of the water or other solvent used to form the flowable adhesive composition intermediate. Removal of the volatile solvent yields an adhesive layer comprising a substantially solid adhesive composition. Thereafter, individual intermediate strips or patches can be separated from the sheet. Alternatively, a solid sheet comprising the adhesive composition or layer can be separated from the polymer sheet and molded, stamped or otherwise formed into strips or patches. Once the intermediate patches or adhesive layers have been formed, the treatment gel may be applied or placed adjacent to an inner surface of the adhesive layer.

In yet another embodiment of the invention, a barrier layer in the form of a strip or patch can be coated with a flowable adhesive composition intermediate. The adhesive composition intermediate is then heated together with the barrier layer in order to form an adhesive layer comprising a substantially solid adhesive composition. Thereafter, a treatment gel is applied to an inner surface of the adhesive layer in order to yield a finished treatment strip or patch according to the invention. Any or all of these assembly processes can be performed during commercial manufacture of the treatment device, or by an end user as part of using a treatment kit.

IV. Methods of Using Treatment Compositions and Treatment Strips Incorporating such Compositions The treatment compositions and strips according to the invention can be designed to be worn for any desired time period. Increasing the concentration of the one or more active agents generally reduces the time required to effect the desired treatment. Nevertheless, due to the extremely comfortable fit and reliable adhesion between the inventive treatment compositions or strip and the person's teeth, it is possible to wear such compositions or strips for extended periods of time in order to ensure more uniform treatment. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive devices such as large, bulky dental appliances.

The treatment compositions or strips according to the invention may be worn over a person's upper dental arch, lower dental arch, or both simultaneously. The ability to reliably and comfortably wear treatment compositions or strips over the upper and lower dental arches simultaneously is another departure from conventional bleaching strips, which are not recommended for use in treating the upper and lower dental arches simultaneously.

Figure 5:
FIG. 5 illustrates a person placing a treatment composition or strip according to the invention over the upper dental arch.
Figure 6:
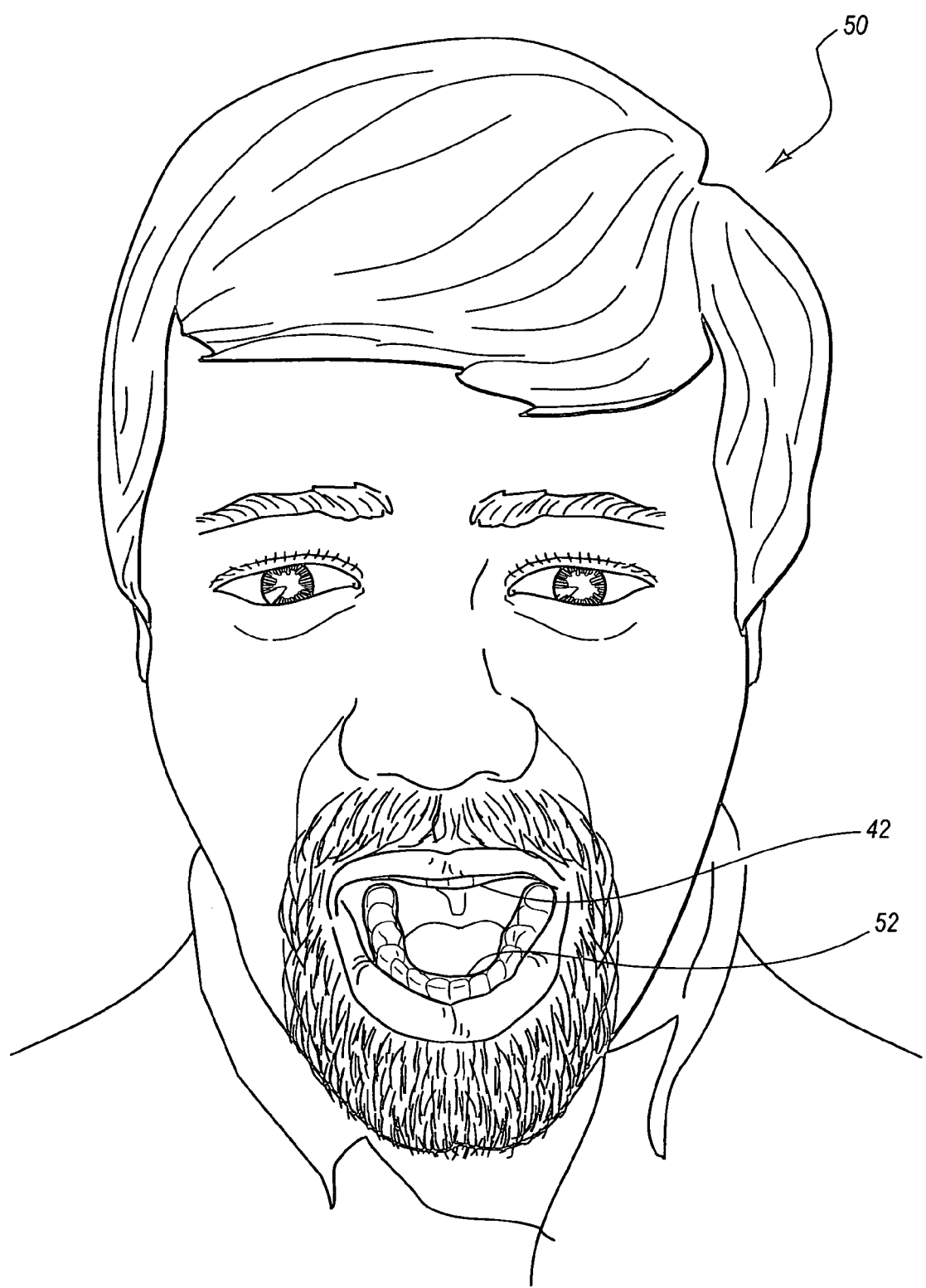
FIG. 6 illustrates a person placing a treatment composition or strip according to the invention over the lower dental arch, with a treatment composition or strip already placed over the upper dental arch.

FIG. 5 illustrates a person 40 placing a treatment composition or strip 42 over the person's upper dental arch. As illustrated in FIG. 4, the treatment strip 42 (or composition) can be bent, curved, folded or otherwise manipulated so as to have a desired shape or cross section (e.g., a U- or V-shaped cross section) so as to facilitate placement of the strip 42 over the person's teeth. FIG. 6 illustrates the person 40 having placed a treatment composition or strip 52 over the person's lower dental arch after having placed the treatment composition or strip 42 over the upper dental arch. It will be appreciated, however, that the treatment compositions or strips can be placed over a person's upper and lower dental arches in any desired order.

To remove the treatment composition or strip, a user can pry open a corner of the barrier layer and/or adhesive layer using a fingernail or rigid tool and then pull the remainder off. Any residual adhesive composition and/or treatment gel that remains adhered to the person's teeth can be removed by washing or flushing water over the person's teeth, and/or by brushing. Although the inventive treatment compositions are very adhesive to teeth when protected from excessive moisture, they can be formulated to quickly break down and dissolve when flushed with excess water and/or by gentle mechanical action (e.g., brushing).

The treatment compositions and strips can be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours.

Treatment sessions according to the invention may be repeated as many times as needed to obtain a desired degree of treatment. In the case of dental bleaching compositions according to the invention, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Treatment Kits

For convenience of use, multiple treatment compositions or strips may be packaged together and sold as a kit. In the case of treatment compositions that do not initially include a barrier layer, a separate barrier layer, or material used to form a barrier layer, may be optionally included within the kit. In one embodiment, the number of treatment compositions or strips provided with each kit may equal the number of sessions that represent a prescribed treatment regimen. Because of the ease of placing the inventive treatment compositions or strips over a person's teeth, coupled with the reliability with which they adhere to teeth, the likelihood that a particular treatment composition or strip will fail, or otherwise not work as intended, is greatly diminished compared to conventional bleaching strips.

To efficiently utilize the space within a kit package, multiple treatment compositions or strips can be stacked or placed together within a package. The treatment compositions or strips can be sealed collectively or individually as desired. A protective package 30 is depicted in FIG. 3. The treatment compositions or strips may optionally contain a removable protective layer on an interior surface to protect the treatment gel and adhesive layer from contamination or moisture.

It is within the scope of the invention to provide barrier layers and treatment compositions that are initially separate and that are brought together by the end user. For example, the treatment composition may comprise a pre-shaped strip or patch placed adjacent to a barrier layer, with or without actually adhering the adhesive layer to the barrier layer. Alternatively, a flowable adhesive composition intermediate can be placed adjacent to a barrier layer and allowed to dry prior to placement of the treatment gel against an inner surface of the substantially solid adhesive layer. Thereafter, a treatment gel is placed adjacent to the inner surface of the substantially solid adhesive layer. A treatment gel may also be placed by a user adjacent to an inner surface of an adhesive layer or composition in the absence of a barrier layer, or prior to placing a barrier layer adjacent to an outer surface of the adhesive layer.

VI. EXAMPLES OF THE PREFERRED EMBODIMENTS

The following are several examples of treatment compositions and treatment strips that have been formulated and manufactured according to the invention. The exemplary formulations and manufacturing conditions are given by way of example, and not by limitation, in order to illustrate treatment compositions and strips that have been found to be useful in treating a person's teeth and/or gums. Unless otherwise indicated, all percentages are by weight.

Examples 1–21 are directed to the manufacture of adhesive dental bleaching layers that become more adhesive when moistened by saliva or water. Examples 22–26 are directed to the manufacture of adhesive dental desensitizing layers that become more adhesive when moistened by saliva or water. Examples 27–29 are directed to the manufacture of adhesive medicament layers that become more adhesive when moistened by saliva or water. The adhesive bleaching, desensitizing and medicament layers of Examples 1–29 therefore comprise exemplary adhesive compositions or layers according to the invention. Accordingly, exemplary treatment compositions or strips according to the invention can be manufactured by placing any treatment gel disclosed herein, or known in the art, adjacent to an inner surface of the adhesive bleaching, desensitizing or medicament layers of Examples 1–29.

Examples 30–35 are directed to the manufacture of adhesive compositions or layers that do not include any active agent. Exemplary treatment compositions or strips according to the invention can be manufactured by placing any treatment gel disclosed herein, or known in the art, adjacent to an inner surface of the adhesive layers of Examples 30–35.

Finally, Examples 36–40 are directed to exemplary treatment gels that are suitable for use in manufacturing treatment compositions or strips according to the invention. For example, treatment compositions or strips according to the invention can be manufactured by placing the bleaching gels of Examples 36–40 adjacent to any of the adhesive layers described herein, including those formed according to Examples 1–35.

Example 1

An initially flowable intermediate composition suitable for use in manufacturing a substantially solid, cohesive, and non-flowable adhesive bleaching layer was formed by mixing together the following components:

| | |
|---|---|
| Carbamide Peroxide | 16% |
| Polyvinyl pyrrolidone (M.W. = 1.3 million) | 38% |
| Water | 46% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The composition was spread using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The dried bleaching layer adhered well to each of the polymer sheets. The coated sheets were placed back into the oven overnight to remove additional water.

The coated sheets were removed from the oven a second time, cut apart into smaller-sized pieces, and shaped into treatment strips suitable for placement over a person's teeth. The treatment strips were tested by placing them over a person's teeth. The residual saliva present on the tooth surfaces moistened the exposed surface of the bleaching layer and caused it to become sticky and very adhesive to teeth almost immediately. The treatment strips were pressed against the teeth, which caused them to conform to the natural irregularities of the dental arch and adhere firmly against the teeth. This demonstrated that the adhesive bleaching layer formed in this example comprises an excellent adhesive layer.

A treatment gel is placed adjacent to an inner surface of the adhesive bleaching layer to yield a treatment strip or patch according to the invention. The treatment gel is not heated prior to placing the treatment strip over a person's teeth, which helps preserves the potency and concentration of the active agent within the treatment gel in the case where the active agent is sensitive to heat.

The treatment strip is worn for varying time periods ranging from several minutes to several hours without becoming dislodged. The formation of oxygen bubbles in the case of a treatment gel comprising a peroxide bleaching agent indicates that the bleaching agent remains active. In some cases a noticeable bleaching effect is detected after just one bleaching session (e.g., a 2-hour bleaching session). Noticeable bleaching is typically detected after 1–3 bleaching sessions.

Example 2

An initially flowable intermediate composition suitable for use in manufacturing a substantially solid, cohesive, and non-flowable adhesive bleaching layer was formed by mixing together the following components:

| | |
|---|---|
| Carbamide Peroxide | 16% |
| PolyOx WSR 101(M.W.= 1 million) | 7% |
| Water | 77% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. Unlike the bleaching layer of Example 1, the bleaching layer of Example 2 did not adhere strongly to the polymer sheets but was easily separated therefrom. The coated sheets were placed back into the oven overnight.

The coated sheets were removed from the oven a second time, cut apart into smaller-sized pieces, and shaped into strips or patches suitable for placement over a person's teeth. The strips or patches were tested by placing them over a person's teeth. The residual saliva present on the tooth surfaces moistened the exposed surface of the solid bleaching layer and caused it to become sticky and adhesive to teeth within a few seconds. The results of Example 2 indicate that, while polyethylene oxide was a satisfactory tooth adhesion agent, it was less satisfactory in promoting adhesion between a solid bleaching layer and a polymer sheet.

A treatment gel is placed adjacent to an inner surface of the adhesive bleaching layer to yield a treatment strip according to the invention that is very adhesive to a person's teeth and/or gums.

Example 3

An initially flowable intermediate composition suitable for use in manufacturing a substantially solid, cohesive, and non-flowable adhesive bleaching layer was formed by mixing together the following components:

| | |
|---|---|
| Carbamide Peroxide | 16% |
| Carbopol 974P | 5% |
| Aqueous NaOH (50%) | 6% |
| Water | 73% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. Although the intermediate composition dried sufficiently to form a solid, it shrunk considerably, probably because of the large amount of water that was needed to cause Carbopol to form a gel. Shrinkage of the intermediate composition caused the polymer sheet to become partially shriveled up. Whereas shriveling of the polymer sheet was not desired, using carboxypolymethylene as a tooth adhesion agent resulted in a dried bleaching composition that adhered to a polymer sheet.

Thereafter, the coated sheets were removed from the oven after heating overnight, cut apart into smaller-sized pieces, and shaped into strips or patches suitable for placement over a person's teeth. When placed over a person's teeth it took about 5 seconds for the solid bleaching layer to become moistened enough to start becoming sticky and adhesive to teeth. The strips or patches were able to conform to the person's teeth and remain in place after being pressed against the teeth for about 30–60 seconds.

The results of Example 3 indicate that, while Carbopol 974 P is able to adhere to a MYLAR sheet and appears to be a satisfactory tooth adhesion agent once the solid adhesive bleaching layer is sufficiently moistened, it presents a shrinkage problem that can cause undesirable deformation of thin, flexible polymer sheets. One would expect Carbopol 974 P to work better when used with less flexible sheets of sufficient rigidity to avoid shriveling or unwanted deformation.

A treatment gel is placed adjacent to an inner surface of the adhesive bleaching layer to yield a treatment strip according to the invention that is very adhesive to a person's teeth and/or gums.

Example 4

An initially flowable intermediate composition suitable for use in manufacturing a substantially solid, cohesive, and non-flowable adhesive bleaching layer was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising an adhesive bleaching layer could also be formed by spreading the intermediate composition on a solid surface such as glass, drying the composition, and then peeling off the dried adhesive layer.

By comparison, when the intermediate composition of Example 1 was applied to a glass surface and then dried, it adhered so strongly that it could not readily be peeled off the glass surface. Instead, it had to be forcefully chipped or pried off using a razor blade.

The solid bleaching layer of Example 4 did, however, adhere to a person's teeth when moistened, although not as well as the solid bleaching layers of Examples 1–3. This indicates that the bleaching layer of Example 4 might have commercial application as an adhesive layer in a treatment strip to the extent that problems adhering to the barrier layer are overcome or are not an issue.

A treatment gel is placed adjacent to an inner surface of the adhesive bleaching layer to yield a treatment strip according to the invention that is very adhesive to a person's teeth and/or gums.

Example 5

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. Using a mixture of water and ethanol as the solvent allowed the intermediate composition to dry in less than time than the intermediate compositions of Examples 1–4. The inclusion of glycerin helped the bleaching layer remain more flexible and less brittle after drying. The bleaching layer adhered well to each of the polymer sheets. After initial drying, the coated sheets were placed back into the oven overnight.

The coated sheets were removed from the oven a second time, cut apart into smaller-sized pieces, and shaped into strips or patches suitable for placement over a person's teeth and/or gums. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 6

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. The inclusion of polyethylene glycol helped the bleaching layer remain more flexible and less brittle after drying. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 7

An initially flowable intermediate composition suitable for use in manufacturing a substantially solid, cohesive, and non-flowable adhesive bleaching layer was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. Using ethanol as the only solvent allowed the intermediate composition to dry in even less time than the compositions of Examples 5 and 6. The barrier layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 8

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The resulting intermediate composition was spread over the surfaces of polyethylene, a paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 9

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 10

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The resulting intermediate composition was spread over the surfaces of polyethylene, paraffin, and MYLAR sheets as described in Example 1. Aerosil 200 was added as a tackifying agent to promote adhesion of the intermediate composition to the polymer sheets. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 11

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 12

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 12 did not adhere well to the MYLAR sheets. It also shrunk somewhat after extended drying. The bleaching layer of Example 12 was able to adhere to a person's teeth when moistened.

A treatment gel is placed adjacent to an inner surface of the adhesive bleaching layer to yield a treatment strip according to the invention that is very adhesive to a person's teeth and/or gums.

Example 13

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent of bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 14

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 15

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 16

An initially flowable intermediate composition suitable for use in manufacturing a substantially solid, cohesive, and non-flowable adhesive bleaching layer was formed by mixing together the following components:

| | |
|---|---|
| Carbamide Peroxide | 15% |
| Polyvinyl pyrrolidone (M.W. = 1.3 million) | 32% |
| Water | 12.8% |
| Ethanol | 20% |
| Glycerin | 10% |
| Aerosil 200 | 5% |
| Calcium EDTA | 0.2% |
| Sodium Lauryl Sulfate | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 17

An initially flowable intermediate composition suitable for use in manufacturing a substantially solid, cohesive, and non-flowable adhesive bleaching layer was formed by mixing together the following components:

| | |
|---|---|
| Carbamide Peroxide | 15% |
| Polyvinyl pyrrolidone (M.W. = 1.3 million) | 26% |
| Water | 16.8% |
| Ethanol | 25% |
| Glycerin | 15% |
| Calcium EDTA | 0.2% |
| Sodium Lauryl Ether Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 18

An initially flowable intermediate composition suitable for use in manufacturing a substantially solid, cohesive, and non-flowable adhesive bleaching layer was formed by mixing together the following components:

| | |
|---|---|
| Carbamide Peroxide | 15% |
| Polyvinyl pyrrolidone (M.W. = 1.3 million) | 32% |
| Water | 13.8% |
| Ethanol | 20% |
| Glycerin | 12% |
| Aerosil 200 | 5% |
| Calcium EDTA | 0.2% |
| Silwet L-7001 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 19

An initially flowable intermediate composition suitable for use in manufacturing a substantially solid, cohesive, and non-flowable adhesive bleaching layer was formed by mixing together the following components:

| | |
|---|---|
| Calcium Peroxide | 20% |
| Carbamide Peroxide | 4% |
| Polyvinyl pyrrolidone (M.W. = 1.3 million) | 20% |
| Water | 11.8% |
| Ethanol | 20% |
| Glycerin | 18% |
| Aerosil 200 | 5% |
| Calcium EDTA | 0.2% |
| Sodium Lauryl Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 20

An initially flowable intermediate composition suitable for use in manufacturing a substantially solid, cohesive, and non-flowable adhesive bleaching layer was formed by mixing together the following components:

| | |
|---|---|
| Carbamide Peroxide | 10% |
| Kollidon 90 (M.W. = 1.3 million) | 18.7% |
| Water | 42.3% |
| Ethanol | 13.3% |
| Glycerin | 12% |
| Aerosil 200 | 3.3% |
| Sodium Lauryl Sulfate | 0.33% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 21

An initially flowable intermediate composition suitable for use in manufacturing a substantially solid, cohesive, and non-flowable adhesive bleaching layer was formed by mixing together the following components:

| | |
|---|---|
| Carbamide Peroxide | 7.1% |
| Kollidon 90 (M.W. = 1.3 million) | 25% |
| Water | 10.7% |
| Ethanol | 50.7% |
| Glycerin | 2.9% |
| Aerosil 200 | 3.6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into strips or patches suitable for placement over a person's teeth. The strips or patches adhered almost immediately when placed over a person's teeth.

A treatment gel is placed adjacent to an inner surface of the adhesive bleaching layer to yield a treatment strip according to the invention that is very adhesive to a person's teeth and/or gums.

Example 22

An initially flowable intermediate composition suitable for use in manufacturing a substantially solid, cohesive, and non-flowable adhesive desensitizing layer was formed by mixing together the following components:

| | |
|---|---:|
| Sodium Fluoride | 0.25% |
| Polyvinyl pyrrolidone (M.W. = 1.3 million) | 30% |
| Water | 69.75% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The intermediate composition was spread using a screeding device. The coated sheets were heated in a forced air oven heated to a temperature of 50–70° C. for approximately 1 hour. The coated sheets were removed from the oven and inspected. The intermediate composition had dried sufficiently so as to form a solid, coherent desensitizing layer on the surface of the polymer sheets. The dried desensitizing composition adhered well to each of the polymer sheets.

The coated sheets were cut apart into smaller-sized pieces and shaped into strips or patches suitable for placement over a person's teeth. The strips or patches were tested by placing them over a person's teeth. The residual saliva present on the tooth surfaces moistened the exposed surface of the desensitizing layer and caused it to become sticky and very adhesive to teeth almost immediately. The strips or patches were pressed against the teeth, which caused them to conform to the natural irregularities of the dental arch and adhere firmly against the teeth. This demonstrated that the desensitizing layer formed in this example comprises an excellent adhesive layer.

A treatment gel is placed adjacent to an inner surface of the adhesive desensitizing layer to yield a treatment strip according to the invention. The treatment strip is worn for varying time periods ranging from several minutes to several hours without becoming dislodged. The sodium fluoride also acts as both a desensitizing agent and a remineralizing agent.

Example 23

An initially flowable intermediate composition suitable for use in manufacturing a substantially solid, cohesive, and non-flowable adhesive desensitizing layer was formed by mixing together the following components:

| | |
|---|---:|
| Sodium Citrate | 5% |
| Polyvinyl pyrrolidone (M.W. = 1.3 million) | 20% |
| Water | 75% |

The resulting intermediate composition was manufactured into strips or patches according to the method described in Example 22. The desensitizing layer adhered well to the barrier layers comprising polymer sheets. The strips or patches were tested by placing them over a person's teeth. The residual saliva present on the tooth surfaces moistened the exposed surface of the desensitizing layer and caused it to become sticky and very adhesive to teeth almost immediately. The strips or patches were pressed against the teeth, which caused them to conform to the natural irregularities of the dental arch and adhere firmly against the teeth.

A treatment gel is placed adjacent to an inner surface of the adhesive desensitizing layer to yield a treatment strip according to the invention that is very adhesive to a person's teeth and/or gums.

Example 24

An initially flowable intermediate composition suitable for use in manufacturing a substantially solid, cohesive, and non-flowable adhesive desensitizing layer was formed by mixing together the following components:

| | |
|---|---:|
| Potassium Nitrate | 3% |
| Polyvinyl pyrrolidone (M.W. = 1.3 million) | 15% |
| Ethanol | 30% |
| Water | 52% |

The resulting intermediate composition was manufactured into strips or patches according to the method described in Example 22. The desensitizing layer adhered well to the barrier layers comprising polymer sheets. The strips or patches were tested by placing them over a person's teeth. The residual saliva present on the tooth surfaces moistened the exposed surface of the desensitizing layer and caused it to become sticky and very adhesive to teeth almost immediately. The strips or patches were pressed against the teeth, which caused them to conform to the natural irregularities of the dental arch and adhere firmly against the teeth.

A treatment gel is placed adjacent to an inner surface of the adhesive desensitizing layer to yield a treatment strip according to the invention that is very adhesive to a person's teeth and/or gums.

Example 25

An initially flowable intermediate composition suitable for use in manufacturing a substantially solid, cohesive, and non-flowable adhesive desensitizing layer was formed by mixing together the following components:

| | |
|---|---:|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The resulting intermediate composition was manufactured into strips or patches according to the method described in Example 22. The desensitizing layer adhered well to the barrier layers comprising polymer sheets. The strips or patches were tested by placing them over a person's teeth. The residual saliva present on the tooth surfaces moistened the exposed surface of the desensitizing layer and caused it to become sticky and very adhesive to teeth almost immediately. The strips or patches were pressed against the teeth, which caused them to conform to the natural irregularities of the dental arch and adhere firmly against the teeth. The sodium fluoride also acts as a remineralizing agent.

A treatment gel is placed adjacent to an inner surface of the adhesive desensitizing layer to yield a treatment strip according to the invention that is very adhesive to a person's teeth and/or gums.

Example 26

An initially flowable intermediate composition suitable for use in manufacturing a substantially solid, cohesive, and non-flowable adhesive bleaching and desensitizing layer was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The resulting intermediate composition was manufactured into strips or patches according to the method described in Example 22. The bleaching and desensitizing layer adhered well to the barrier layers comprising polymer sheets. The strips or patches were tested by placing them over a person's teeth. The residual saliva present on the tooth surfaces moistened the exposed surface of the desensitizing layer and caused it to become sticky and very adhesive to teeth almost immediately. The strips or patches were pressed against the teeth, which caused them to conform to the natural irregularities of the dental arch and adhere firmly against the teeth. The sodium fluoride also acts as a remineralizing agent.

A treatment gel is placed adjacent to an inner surface of the adhesive desensitizing layer to yield a treatment strip according to the invention that is very adhesive to a person's teeth and/or gums.

Example 27

An initially flowable medicament composition suitable for use in manufacturing a substantially solid, cohesive, and non-flowable adhesive medicament layer was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The resulting medicament composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The medicament composition was spread using a screeding device. The coated sheets were heated in a forced air oven heated to a temperature of 50–70° C. for approximately 1 hour. The coated sheets were removed from the oven and inspected. The medicament composition had dried sufficiently so as to form a solid, coherent medicament layer on the surface of the polymer sheets. The dried medicament composition adhered well to each of the polymer sheets.

The coated sheets were removed from the oven a second time, cut apart into smaller-sized pieces, and shaped into strips or patches suitable for placement over a person's teeth and/or gingiva. The strips or patches were tested by placing them over a person's teeth and/or gingiva. The residual saliva present on the tooth and/or gingival surfaces moistened the exposed surface of the dry medicament composition and caused it to become sticky and very adhesive to teeth and/or gingiva almost immediately. The treatment strips were pressed against the teeth and/or gingiva, which caused them to conform to the natural irregularities of the dental arch and adhere firmly against the teeth and/or gingival surfaces.

The treatment strips were worn for varying time periods ranging from several minutes to several hours without becoming dislodged. Such devices are suitable for use in treating periodontal disease and other infections of oral tissues that respond to topical applications of antimicrobial compositions such as chlorhexidine gluconate.

Example 28

An initially flowable medicament composition suitable for use in manufacturing a substantially solid, cohesive, and non-flowable adhesive medicament layer was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The resulting intermediate composition was manufactured into strips or patches according to the method described in Example 27. The medicament layer adhered well to the barrier layers comprising polymer sheets. The strips or patches were tested by placing them over a person's teeth and/or gums. The residual saliva present on the tooth and/or gum surfaces moistened the exposed surface of the desensitizing layer and caused it to become sticky and very adhesive to teeth and/or gums almost immediately. The strips or patches were pressed against the teeth and/or gums, which caused them to conform to the natural irregularities of the dental arch and adhere firmly against the teeth and/or gums.

A treatment gel is placed adjacent to an inner surface of the adhesive medicament layer to yield a treatment strip according to the invention that is very adhesive to a person's teeth and/or gums.

Example 29

An initially flowable medicament composition suitable for use in manufacturing a substantially solid, cohesive, and non-flowable adhesive medicament layer was formed by mixing together the following components:

| | |
|---|---|
| Phenol | 3% |
| Polyvinyl pyrrolidone (M.W. = 1.3 million) | 35% |
| Ethanol | 62% |

The resulting intermediate composition was manufactured into strips or patches according to the method described in Example 27. The medicament layer adhered well to the barrier layers comprising polymer sheets. The strips or patches were tested by placing them over a person's teeth and/or gums. The residual saliva present on the tooth and/or gum surfaces moistened the exposed surface of the desensitizing layer and caused it to become sticky and very adhesive to teeth and/or gums almost immediately. The strips or patches were pressed against the teeth and/or gums, which caused them to conform to the natural irregularities of the dental arch and adhere firmly against the teeth and/or gums.

A treatment gel is placed adjacent to an inner surface of the adhesive medicament layer to yield a treatment strip according to the invention that is very adhesive to a person's teeth and/or gums.

Example 30

An initially flowable adhesive composition intermediate suitable for use in manufacturing a substantially solid adhesive layer was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 31

An initially flowable adhesive composition intermediate suitable for use in manufacturing a substantially solid adhesive layer was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 32

An initially flowable adhesive composition intermediate suitable for use in manufacturing a substantially solid adhesive layer was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 33

An initially flowable adhesive composition intermediate suitable for use in manufacturing a substantially solid adhesive layer was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 34

An initially flowable adhesive composition intermediate suitable for use in manufacturing a substantially solid adhesive layer was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 35

An initially flowable adhesive composition intermediate suitable for use in manufacturing a substantially solid adhesive layer was formed by mixing together the following components:

| | |
|---|---|
| Ethanol | 63.6% |
| Glycerin | 9.1% |
| Polyvinyl pyrrolidone (M.W. = 1.3 million) | 27.3% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 36

An initially flowable adhesive composition intermediate suitable for use in manufacturing a substantially solid adhesive layer was formed by mixing together the following components:

| | |
|---|---|
| Ethanol | 44% |
| Polyvinyl pyrrolidone (M.W. = 1.3 million) | 34% |
| Glycerin | 14% |
| Sodium Lauryl Sulfate | 3% |
| Sucralose | 1% |
| Artificial Peach Flavor | 4% |

The resulting adhesive composition intermediate was manufactured into treatment strips or intermediate strips or patches according to the methods described in Examples 1, 22 or 27. The adhesive layer adhered well to the barrier layers comprising polymer sheets.

A treatment gel is placed adjacent to an inner surface of the adhesive layer to yield a treatment strip according to the invention that is very adhesive to a person's teeth and/or gums.

Example 37

A treatment gel suitable for use in manufacturing treatment compositions and strips according to the invention was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 (SiO$_2$) | 7% |

-continued

| | |
|---|---|
| Peach Flavor | 2% |
| Polyethylene Glycol (M.W. = 20,000) | 20% |

The resulting treatment gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more). Like any dental tray filled with a conventional dental bleaching composition, the dental tray of this example was easily dislodged from the person's mouth. Moreover, the bleaching gel was easily expressed out of the dental tray and into the person's oral cavity by normal mouth movements, such as talking, yawning or clenching of teeth. The result would have been expected to be as bad or worse in the case where the treatment gel is placed adjacent to a flat barrier layer to form a bleaching strip that does not include a solid adhesive layer.

Thereafter, the treatment gel was used to form treatment devices by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity. One reason for this was the much stronger seal between the adhesive layer and the person's teeth than is possible when using the treatment gel and a dental tray or flat barrier layer only. Another reason was that the strong adhesion between the adhesive layer and the person's teeth greatly diminished the freedom of movement of the bleaching device relative to the person's teeth.

Example 38

A treatment gel suitable for use in manufacturing treatment compositions and strips according to the invention was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The resulting treatment gel was extremely thick. The treatment gel was used to form treatment devices according to the invention by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity.

Example 39

A treatment gel suitable for use in manufacturing treatment compositions and strips according to the invention was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The resulting treatment gel had a very good consistency and was able to be easily loaded into a dental tray and then hold the dental tray against a person's teeth. The treatment gel was used to form treatment devices according to the invention by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity.

Example 40

A treatment gel suitable for use in manufacturing treatment compositions and strips according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The resulting treatment gel had a very good consistency and was able to be easily loaded into a dental tray and then hold the dental tray against a person's teeth. The treatment gel was used to form treatment devices according to the invention by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity.

Example 41

A treatment gel suitable for use in manufacturing treatment compositions and strips according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The resulting treatment gel had a very good consistency and was able to be easily loaded into a dental tray and then hold the dental tray against a person's teeth. The treatment gel was used to form treatment devices according to the invention by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity.

Example 42

A treatment gel suitable for use in manufacturing treatment compositions and strips according to the invention was formed by mixing together the following components:

| | |
|---|---|
| Water | 22.5% |
| EDTA Disodium | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone | 2% |
| Carboxy Methyl Cellulose | 4% |
| Artificial Peach Flavor | 3% |

The resulting treatment gel had a very good consistency and was able to be easily loaded into a dental tray and then hold the dental tray against a person's teeth. The treatment gel was used to form treatment devices according to the invention by being placed adjacent to one or more adhesive layers of Examples 30–36. A treatment device was tested by placing it over a person's teeth. The treatment device adhered very strongly to the person's teeth such that it could only be dislodged by intentionally pealing it off the person's teeth. The treatment gel was firmly held between the barrier layer and the person's teeth such that it did not readily spill out of the treatment device and into the person's oral cavity.

Example 43

Any of the treatment gels of Examples 37–42 are placed adjacent to an inner surface of any of the adhesive layers of Examples 1–29 in order to form treatment compositions and strips according to the invention.

Example 44

Any of the treatment gels of Examples 37–42 are modified by adding one or more of a desensitizing agent, remineralizing agent, an antimicrobial agent, an antiplaque agent, an anti-tartar agent, or other medicament in addition to, or instead of, the bleaching agent to yield a treatment gel having desired properties.

Example 45

Any of the foregoing compositions or strips are modified by including, adjacent to one of the adhesive layers, one or more treatment gels disclosed in one or more of the following U.S. Patents: U.S. Pat. No. 5,376,006; U.S. Pat. No. 5,770,182; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; and U.S. Pat. No. 6,503,485.

Example 46

Dental treatment devices are manufactured by placing any of the adhesive compositions or layers according to Examples 1–36 adjacent to a strip or patch comprising a blend of ethyl vinyl acetate (80%) and polypropylene (20%) and placing a treatment gel according to any of Examples 37–42 and 44–45 adjacent to a surface of the adhesive composition or layer opposite the strip or patch.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. In a dental treatment system that includes a moisture-resistant barrier layer adapted to be placed upon and worn over a treatment composition used in treating a person's teeth, an improved treatment composition in the form of a strip or patch comprising:
    an adhesive layer comprising a substantially dry adhesive composition that is sufficiently solid so that it will substantially maintain a strip-like configuration so as to be adapted for handling and application to a patient's teeth either with or independent of the barrier layer, the adhesive layer having increased adhesiveness to teeth when moistened by saliva or water and comprising at least one tooth adhesion agent that at least partially contributes to said increased adhesiveness to teeth; and
    a substantially viscous and tacky treatment gel, adjacent to said adhesive layer, comprising at least one active agent, at least one tackifying agent, and a liquid or gel carrier.

2. A treatment composition as defined in claim 1, said adhesive layer being substantially flat prior to placing the treatment composition over a person's teeth and/or gums.

3. A treatment composition as defined in claim 1, said adhesive layer being curved or bent prior to placing the treatment composition over a person's teeth and/or gums.

4. A treatment composition as defined in claim 1, the treatment composition being curved in at least one of a lengthwise or widthwise direction.

5. A treatment composition as defined in claim 1, the treatment composition sized and configured so as to fit over at least a portion of a person's upper dental arch.

6. A treatment composition as defined in claim 1, the treatment composition sized and configured so as to fit over at least a portion of a person's lower dental arch.

7. A treatment composition as defined in claim 1, wherein the treatment composition is sized and configured so as to approximately terminate at or near a person's gingival margin when in use.

8. A treatment composition as defined in claim 1, said tooth adhesion agent comprising polyvinyl pyrrolidone.

9. A treatment composition as defined in claim 1, said tooth adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

10. A treatment composition as defined in claim 1, said tooth adhesion agent having a concentration in a range of about 10% to about 90% by weight of said adhesive composition.

11. A treatment composition as defined in claim 1, said tooth adhesion agent having a concentration in a range of about 20% to about 80% by weight of said adhesive composition.

12. A treatment composition as defined in claim 1, said tooth adhesion agent having a concentration in a range of about 40% to about 75% by weight of said adhesive composition.

13. A treatment composition as defined in claim 1, said adhesive composition further comprising at least one humectant.

14. A treatment composition as defined in claim 1, wherein said adhesive layer has a cross-sectional thickness in a range of about 0.1 mm to about 0.5 mm.

15. A treatment composition as defined in claim 1, wherein said adhesive layer has a cross-sectional thickness in a range of about 0.5 mm to about 2 mm.

16. A treatment composition as defined in claim 1, wherein said adhesive layer has a cross-sectional thickness in a range of about 2 mm to about 3 mm.

17. A treatment composition as defined in claim 1, said adhesive composition further comprising at least one member selected from the group comprising dental bleaching agents, dental desensitizing agents, remineralizing agent, antimicrobial agents, antiplaque agents, and anti-tartar agents.

18. A treatment composition as defined in claim 1, said active agent comprising at least one member selected from the group comprising dental desensitizing agents, remineralizing agent, antimicrobial agents, antiplaque agents, and anti-tartar agents.

19. A treatment composition as defined in claim 1, said active agent comprising at least one dental bleaching agent.

20. A treatment composition as defined in claim 1, said dental bleaching agent having a concentration in a range of about 1% to about 60% by weight of said treatment gel.

21. A treatment composition as defined in claim 1, said dental bleaching agent having a concentration in a range of about 3% to about 40% by weight of said treatment gel.

22. A treatment composition as defined in claim 1, said dental bleaching agent having a concentration in a range of about 5% to about 30% by weight of said treatment gel.

23. A treatment composition as defined in claim 1, said tackifying agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

24. A treatment composition as defined in claim 1, further comprising a barrier layer comprising a moisture-resistant material adjacent to an opposite surface of said adhesive layer that protects the adhesive layer and treatment gel from saliva or moisture when the treatment composition is in use.

25. A treatment composition as defined in claim 24, said barrier layer being flexible so that it will readily conform to the shape of a person's teeth when in use.

26. A treatment composition as defined in claim 24, said barrier layer comprising at least one polyolefin.

27. A treatment composition as defined in claim 26, said polyolefin comprising at least one of polyethylene, high density polyethylene, low density polyethylene, ultra-low density polyethylene, polypropylene, or polytetrafluoroethylene.

28. A treatment composition as defined in claim 24, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

29. A treatment composition as defined in claim 24, said barrier layer having a cross-sectional thickness in a range of about 0.025 mm to about 1.5 mm.

30. A treatment composition as defined in claim 24, said barrier layer having a cross-sectional thickness in a range of about 0.05 mm to about 1 mm.

31. A treatment composition as defined in claim 1, wherein the strip or patch is contained within a sealed package prior to use.

32. A kit for use in treating a person's teeth comprising a plurality of the treatment compositions according to claim 1.

33. A kit as defined in claim 32, further comprising a barrier layer, or a material used to make a barrier layer, that is positioned adjacent to the adhesive layer when the treatment composition is in use.

34. A method for treating a person's teeth and/or gums comprising obtaining a treatment composition according to claim 1 and placing the treatment composition over at least a portion of the person's teeth and/or gums for a desired time period.

35. A treatment strip or patch for use in treating a person's teeth, comprising:
   a barrier layer comprising a moisture-resistant material; and
   a treatment composition adjacent to said barrier layer comprising:
      an adhesive layer comprising a substantially dry adhesive composition that is sufficiently solid so that it will substantially maintain a strip-like configuration so as to be adapted for handling and application to a patient's teeth either with or independent of the barrier layer, the adhesive layer having increased adhesiveness to teeth when moistened by saliva or water and comprising at least one tooth adhesion agent that at least partially contributes to said increased adhesiveness to teeth; and
      a treatment gel, adjacent to an inner surface of said adhesive layer, comprising at least one active agent, at least one tackifying agent, and a liquid or gel carrier.

36. A treatment strip or patch as defined in claim 35, said barrier layer and said adhesive layer being substantially flat prior to placing the strip or patch over a person's teeth and/or gums.

37. A treatment strip or patch as defined in claim 35, said barrier layer and said adhesive layer being curved or bent prior to placing the strip or patch over a person's teeth and/or gums.

38. A treatment strip or patch as defined in claim 35, said barrier layer and said adhesive layer being curved in at least one of a lengthwise or widthwise direction.

39. A treatment strip or patch as defined in claim 35, said barrier layer being flexible so that it will readily conform to the shape of a person's teeth when in use.

40. A treatment strip or patch as defined in claim 39, said active agent comprising at least one member selected from the group comprising dental desensitizing agents, remineralizing agent, antimicrobial agents, antiplaque agents, and anti-tartar agents.

41. A treatment strip or patch as defined in claim 39, said active agent comprising at least one dental bleaching agent.

42. A treatment strip or patch as defined in claim 39, said adhesive layer comprising a continuous adhesive composition.

43. A treatment strip or patch as defined in claim 39, said adhesive layer comprising a plurality of discontinuous regions of said adhesive compositions.

44. A treatment strip or patch as defined in claim 39, said treatment gel covering the entire inner surface of said adhesive layer.

45. A treatment strip or patch as defined in claim 39, said treatment gel covering a portion of the inner surface of said adhesive layer.

46. A treatment strip or patch as defined in claim 45, said treatment gel comprising a plurality of spaced-apart regions of said treatment gel.

47. A kit for use in treating a person's teeth comprising a plurality of the treatment strips or patches of claim 39.

48. A method for treating a person's teeth comprising obtaining the treatment strip or patch of claim 39 and then placing the treatment strip or patch over at least a portion of the person's teeth and/or gums for a desired time period.

49. A treatment strip or patch as defined in claim 35, said barrier layer comprising at least one polyolefin.

50. A treatment strip or patch as defined in claim 49, said polyolefin comprising at least one of polyethylene, high density polyethylene, low density polyethylene, ultra-low density polyethylene, polypropylene, or polytetrafluoroethylene.

51. A treatment strip or patch as defined in claim 35, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

52. A treatment strip or patch as defined in claim 35, said barrier layer comprising a thin, flexible membrane having no predefined shape, said adhesive layer having sufficiently rigidity so as to at least partially contribute to maintaining said barrier layer in the shape of a strip or patch prior to use.

53. A treatment strip or patch as defined in claim 35, said tooth adhesion agent comprising polyvinyl pyrrolidone.

54. A treatment strip or patch as defined in claim 35, said adhesive composition further comprising at least one member selected from the group comprising dental bleaching agents, dental desensitizing agents, remineralizing agent antimicrobial agents, antiplaque agents, and anti-tartar agents.

55. A method of manufacturing a dental treatment composition for use in a strip or patch for use in treating a person's teeth and/or gums, comprising:

mixing together a tooth adhesion agent and a solvent to form an adhesive composition intermediate;

removing at least a portion of said solvent from said adhesive composition intermediate so as to form an adhesive layer that is substantially dry and is sufficiently solid so that it will substantially maintain a strip-like configuration so as to be adapted for handling and application to a patient's teeth either with or independent of a moisture-resistant barrier layer, said tooth adhesion agent at least partially contributing to increased adhesiveness to teeth when moistened with saliva or water; and placing a substantially viscous and tacky treatment gel adjacent to the adhesive layer for application to the patient's teeth when the adhesive layer is placed on and worn on the teeth under a moisture-resistant barrier layer.

56. A method as defined in claim 55, further comprising placing or forming a barrier layer adjacent to said adhesive layer.

57. A method as defined in claim 55, wherein said barrier layer comprises a flexible sheet.

* * * * *

UNITED STATES PATENT AND TRADEMARK OFFICE
CERTIFICATE OF CORRECTION

PATENT NO. : 6,997,708 B2  
APPLICATION NO. : 10/728525  
DATED : February 14, 2006  
INVENTOR(S) : Allred et al.

It is certified that error appears in the above-identified patent and that said Letters Patent is hereby corrected as shown below:

Column 21  
Line 67, change "preserves" to --preserve--

Column 24  
Line 44, before "time" remove [than]

Column 28  
Line 56, before "bleaching" remove [of]

Signed and Sealed this

Twenty-second Day of August, 2006

JON W. DUDAS  
*Director of the United States Patent and Trademark Office*